(12) United States Patent
Della Ciana

(10) Patent No.: US 7,855,287 B2
(45) Date of Patent: Dec. 21, 2010

(54) PREPARATION OF HIGH PURITY PHENOTHIAZINE N-ALKYLSULFONATES AND THEIR USE IN CHEMILUMINESCENT ASSAYS FOR THE MEASUREMENT OF PEROXIDASE ACTIVITY

(75) Inventor: Leopoldo Della Ciana, Bologna (IT)

(73) Assignee: Cyanagen Srl, Bologna (IT)

( * ) Notice: Subject to any disclaimer, the term of this patent is extended or adjusted under 35 U.S.C. 154(b) by 377 days.

(21) Appl. No.: 12/010,306

(22) Filed: Jan. 23, 2008

(65) Prior Publication Data

US 2008/0176251 A1    Jul. 24, 2008

(30) Foreign Application Priority Data

Jan. 24, 2007   (IT)   .......................... BO2007A0037

(51) Int. Cl.
*C07D 279/26*   (2006.01)
(52) U.S. Cl. .......................................... 544/35; 544/38
(58) Field of Classification Search ................... 544/35, 544/38
See application file for complete search history.

(56) References Cited

U.S. PATENT DOCUMENTS

| 5,171,668 | A | 12/1992 | Sugiyama |
| 6,432,662 | B1 | 8/2002 | Davis et al. |
| 2002/0192736 | A1 | 12/2002 | Davis et al. |

OTHER PUBLICATIONS

Motsenbocker, M.A., et al, J Biolumin Chemilumin 1994; 9: 15-20, "Improvements to Enhanced Horseradish Peroxidase Detection Sensitivity."

Kawanishi, Y., et al, J. Phys. Chem. 1986, 90, 2469-2475, "Coulombic Effect of Photoinduced Electron-Transfer Reactions between Phenothiazines and Viologens."

Sakaguchi, M., et al, J. Phys. Chem. 1990, 94, 870-874, "Photoionization of Alkylphenothiazines in Vesicles: Effects of the Alkyl Chain Length and the Vesicle Surface Charge."

Bodea, C., et al, The Chemistry of Phenothiazines, 1968; 9:322-460, "Advances in Heterocyclic Chemistry."

European Search Report, dated Jun. 19, 2008.

Kawanishi, Y., et al, J. Phys. Chem. 1986, 90, 2469-2475, "Coulombic Effect of Photoinduced Electron-Transfer Reactions between Phenothiazines and Viologens." XP002480454.

Kulys, J. et al, *Electroanalysis*, 18(18), 1771-1777 CODEN: ELANEU; ISSN: 1040-0397, 2006, XP002480455; "Spectroelectrochemical study of N-substituted phenoxazines as electrochemical labels of biomolecules."

Sakaguchi, M., et al, J. Phys. Chem. 94(2), 870-874 CODEN: JPCHAX; ISSN: 0022-3654, 1990, XP002480594; "Photoionization of Alkylphenothiazines in Vesicles: Effects of the Alkyl Chain Length and the Vesicle Surface Charge."

*Primary Examiner*—Kahsay T Habte
(74) *Attorney, Agent, or Firm*—Nixon & Vanderhye P.C.

(57) ABSTRACT

A process is described for preparing, efficiently and with a high degree of purity N-alkylsulfonates of phenothiazine. The process consists in (a) the preparation of the phenothiazine anion, and (b) the reaction of said anion with cyclic alkyl sulfonates, such as 1,3-propane sultone and 1,4-butane sultone. This process is simpler, more direct, and more efficient than the procedures currently used for the synthesis of N-alkylsulfonates derivatives of phenothiazine. In addition, the products obtained with this process are far more pure than those obtained through current procedures and therefore ideal for bioanalytical applications that require high sensitivity, such as assays based on the measurement of peroxidase activity using chemiluminescence.

12 Claims, 2 Drawing Sheets

PREPARATION OF HIGH PURITY PHENOTHIAZINE N-ALKYLSULFONATES AND THEIR USE IN CHEMILUMINESCENT ASSAYS FOR THE MEASUREMENT OF PEROXIDASE ACTIVITY

Water soluble derivatives of phenothiazine, and especially the N-alkylsulfonates described in the present invention, are useful compounds for several commercial applications, including their use as reagents for chemical and biological assays, and in particular as enhancers of the activity of the peroxidase enzyme in chemiluminescent assays with luminol, and as accelerators in peroxidase/accelerator systems in the composition of detergents and in systems for the conversion of solar energy into chemical or electrical energy.

The class of compounds concerning the present invention can be represented by the formula (I):

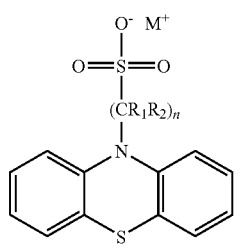

where $M^+$ is a cation and n is an integer. The cation may be $H^+$, a monovalent cation (such as $H^+$, $Na^+$, $Li^+$, $K^+$, $NH_4^+$), another inorganic cation, an organic cation, etc. or a polyvalent cation (including divalent cations) where the remaining charge is neutralised by other anions (e.g., halides, nitrates, sulfates, phosphates) or it may form multiple salts with other molecules of phenothiazine N-alkylsulfonates.

The alkyl chain —$(CR_1R_2)_n$— connecting the sulfonic group to the phenothiazine nitrogen may contain any number of methylene groups $\geq 2$, although n=3 (propyl) and n=4 (butyl) are especially preferred. The methylene groups $CR_1R_2$ in the alkyl chain can be disubstituted, monosubstituted or non-substituted.

This class of compounds is relatively expensive, especially because the current synthetic procedures are inefficient. In addition, and more significantly, the products prepared according to the current procedures are very difficult to obtain in the extremely pure form required by immunoenzymatic assays based on the determination of peroxidase activity by chemiluminescence.

A synthetic procedure for the synthesis of sodium 3-(phenothiazin-10-yl)propane-1-sulfonate is described by Y. Kawanishi, N. Kitamura and S. Tazuke, J. in "Coulombic Effect of Photoinduced Electron-Transfer Reactions between Phenothiazines and Viologens", J. Phys. Chem. 1986; 90:2469-2475. This method requires two steps:

(1) The sodium salt of phenothiazine is reacted with an excess of 1,3-dibromopropane. The product, 10-(3-bromopropyl)phenothiazine is obtained with a 18% yield after purification by column chromatography ($Al_2O_3$/hexane).

(2) The purified 10-(3-bromopropyl)phenothiazine is reacted with a slight excess of sodium sulfite in acetonitrile-water (4/1 v/v). The solvent is removed and the crude product is dissolved in a small amount of methanol and reprecipitated with dry benzene. The precipitate is collected on a filter, dried and purified by gel chromatography. The purified product, sodium 3-(phenothiazin-10-yl)propane-1-sulfonate, is obtained with a 51% yield.

According to this method, the desired product, sodium 3-(phenothiazin-10-yl)propane-1-sulfonate, is obtained with a total yield of only 9%, and with massive use of expensive chromatographic methods. A similar procedure is also described by M. Sakaguchi, M. Hu and L. K, in "Photoionization of Alkylphenothiazines in Vescicles: Effects of the Alkyl Chain Length and the Vesicle Surface Charge", J. Phys. Chem., 1990; 94:870-874; the yield is not shown).

In U.S. Pat. No. 5,171,668 "Method of the Chemiluminescence Assays of the Activity of Peroxidase", assigned to Fujirebio, is described for the first time the use of N-alkylsulfonate derivatives of phenothiazines, and in particular of sodium 3-(phenothiazin-10-yl)propane-1-sulfonate, as enhancers of luminol chemiluminescence. This patent does not contain any specific description of the procedure for the preparation of the N-alkylsulfonate derivatives of phenothiazines employed as enhancers, but merely refers to the general synthetic methods of phenothiazines reported in Bodea et al., Advances in Heterocyclic Chemistry, 1968; 9:322-460. The results obtained by Fujirebio with N-alkylsulfonate derivatives of phenothiazines, and in particular with sodium 3-(phenothiazine-10-yl)propane-1-sulfonate, are not significantly better than those observed with a standard enhancer such as 4-iodophenol, except for a vaguely defined "greater reproducibility".

In contrast, U.S. Pat. No. 6,432,662, "Assay of Peroxidase Activity", assigned to Pierce, describes a method for the assay of peroxidase activity, which, while using the same enhancers as those described in the Fujirebio U.S. Pat. No. 5,171,668, and in particular sodium 3-(phenothiazin-10-yl)propane-1-sulfonate, is claimed to offer a much superior performance in terms of chemiluminescent signal intensity and kinetics. According to U.S. Pat. No. 6,432,662, such difference in performance is attributed to the presence of impurities in the enhancer. In particular, the presence of phenothiazine in the enhancer deactivates the peroxidase enzyme and is therefore extremely detrimental to the production of the chemiluminescent signal.

The method described in U.S. Pat. No. 6,432,662 for the preparation of the enhancer, sodium 3-(phenothiazin-10-yl)propane-1-sulfonate, is the previously mentioned procedure by Y. Kawanishi, N. Kitamura and S. Tazuke. In addition, according to U.S. Pat. No. 6,432,662, the product obtained with this procedure contains "impurities, or traces of impurities that cannot be eliminated by conventional methods known to the art," without revealing any specific method of purification.

On the other hand, it should be stressed that the need to use high purity materials in substrates for chemiluminescence is widely known.

For example, the article by M. A. Motsenbocker and K. Kondo, "Improvements to Enhanced Horseradish Peroxidase Detection Sensitivity" J. Biolum. Chemilumin., 1994; 9:15-20 (1994) states that: "The results are consistent with a simple interference mechanism whereby the enhancer radicals produced by the enzyme are preferentially neutralised by contaminants in the luminol, in the enhancer and in the solvent used to solubilise the enhancer. Consumption of these intereferents delays the emission of light and reduces the limit of detection of peroxidase (HRP)".

It is clear that the method of synthesis of sodium 3-(phenotiazin-10-yl)propane-1-sulphonate initially described by Y. Kawanishi, N. Kitamura and S. Tazuke and subsequently used in U.S. Pat. No. 6,432,662 is not only inefficient (yield 9%), but generates a product contaminated with impurities which are very difficult to eliminate. The presence of these impurities is incompatible with the use of sodium 3-(phenothiazine-10-yl)propane-1-sulfonate as enhancer of chemiluminescence in assays for the determination of peroxidase.

BRIEF DESCRIPTION OF THE INVENTION

An object of this invention is a new method for the synthesis of N-alkylsulfonate derivatives of phenothiazine of exceptional purity and in high yields. The method consists in the reaction of the phenothiazine anion with an alkyl sultone (cyclical sulfone) in an appropriate solvent.

The process is simple and straightforward, based on the crystallization of pure product from the reaction mixture. On the contrary, the impurities remain in solution and then are removed in a very simple and effective way.

The extraordinary purity of N-alkylsulfonate derivatives of phenothiazine obtained by the method of the present invention is of vital importance for their use as enhancers of chemiluminescence in assays of the peroxidase. This is a further object of this invention.

DETAILED DESCRIPTION OF THE INVENTION

Figure 1:
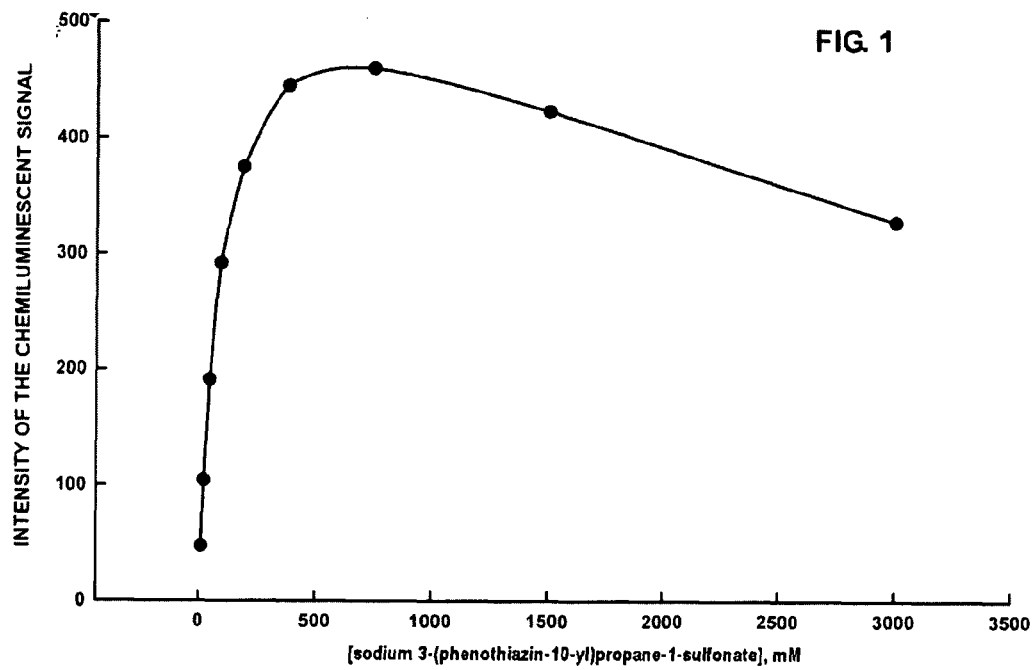
FIG. 1: graph of the chemiluminescent signal as a function of [sodium 3-(phenotiazin-10-yl)propan-1-sulfonate] concentration.

In contrast to literature method, which requires two steps, the procedure of the present invention requires only one step.

In particular, the anion of phenothiazine is generated in situ by addition of a base such as sodium hydride, sodium amide, butyl lithium, lithium diisopropylamide and the like, in an appropriate solvent such as tetrahydrofuran, diethyl ether, t-butylmethyl ether, dioxane, the dimethyl or diethyl ether of ethylene glycol, the dimethyl or diethyl ether of ethylene diglycol, and other similar solvents.

A cyclic alkylsulfonic ester, also known as sultone, is then added, neat or dissolved in a solvent. The alkyl chain, $[-(CR_1R_2)_n-]$, in the alkylsulfonic ester can be a simple non-substituted alkyl chain, $[-(CH_2)_n-]$, where $n = \geq 2$, or the hydrogen atoms can be partially or completely substituted.

Typical substituents are alkyl groups, especially methyl groups, fluorine atoms, trifluoromethyl groups, methyl, ethyl or alkyl ethers. Simple, non-substituted alkyl chains are preferred. Cyclic alkylsulfonate esters with n=3 (1,3-propane sultone) and n=4 (1,4-butane sultone) are especially preferred.

At the end of the reaction the product often separates from the solution in crystalline form and with a high degree of purity. If an even greater degree of purity is desired, it is sufficient to recrystallise the product from ethanol, water, or mixtures thereof.

Other alkyl sultones can be used, including 1-(2-ethoxy-1,1,3,3,3-pentafluoro)propane sultone, which can be prepared by reaction of sulfur trioxide with fluorinated alkenes. Similarly one can use other sultones available from the reaction of alkenes and dienes with $SO_3$-dioxane. For example, 2,3,3-trimethylbutene reacts with $SO_3$-dioxane to give 1-(2,3,3-trimethyl)butane-3-sultone.

The products obtained by the method of the present invention, and in particular sodium 3-(phenothiazin-10-yl)propane-1-sulfonate and sodium 4-(phenothiazin-10-yl)butane-1-sulfonate are of very high purity. In particular, they are totally free from traces of phenothiazine, which causes inactivation of peroxidase enzymes, such as horseradish peroxidase.

The extraordinary purity of sodium 3-(phenothiazin-10-yl)propane-1-sulfonate and sodium 4-(phenothiazin-10-yl)butane-1-sulfonate obtained by the method of the present invention allows them to be used as enhancers of chemiluminescence even in considerably large amounts. For example, a typical substrate for the chemiluminescent detection of peroxidase contains (a) the sodium salt of luminol preferably at a concentration between 2 and 12 mM, more preferably at a concentration between 5 and 10 mM; in addition, it contains (b) an enhancer sodium 3-(phenothiazin-10-yl)propane-1-sulfonate and sodium 4-(phenothiazin-10-yl)butane-1-sulfonate, prepared according to this invention, at a concentration between 2 and 8 mM, more preferably at a concentration between 3 and 6 mM; and also (c) a source of peroxide, preferably at a concentration between 2 and 10 mM, and more preferably at a concentration between 4 and 8 mM.

The substrate solution, also known as working solution, is buffered preferably between pH 7.8 and 9.0, more preferably between pH 8.2 and pH 8.8. The buffer can be Tris, tricine, ecc.

The substrate solution can be prepared just before use, or else it can be obtained by mixing two solutions one containing luminol and the enhancer and the other the source of peroxide. Once prepared, the stability of the solution is limited to about 24 hours, if maintained at 4-8° C. An especially preferred formulation consists of:

Solution A: sodium luminol, 10.0 mM; sodium 3-(phenothiazin-10-yl)propane-1-sulfonate, 6.0 mM in Tris buffer 0.3 M, pH 9.6

Solution B: sodium perborate 8.0 mM in acetate buffer 50 mM, pH 5.0

Both solutions are stable for at least 12 months at 4-8° C. The working solution is prepared just before use by mixing equal volumes of Solutions A and B. The pH of the mixture must be between pH 8.4 and pH 8.7. However, we must bear in mind that since the chemiluminescent reaction is influenced by the concentration of luminol, of the enhancer and pH, it is necessary to optimize the composition of the substrate depending on the application.

The chemiluminescent substrate thus obtained can be used in a large number of chemiluminescent assays of horseradish peroxidase, both in solution and in blotting applications, including Western Blot, Dot Blot, Southern Blot, and Northern Blot assays or any other membrane system that uses horseradish peroxidase, or other peroxidases, as a marker enzyme for the quantification of antigens, antibodies and nucleic acids.

EXAMPLES

The following examples serve to illustrate specific aspects of the invention. However, they are not intended to limit the invention.

Example 1

Synthesis of sodium 3-(phenothiazin-10-yl)propane-1-sulfonate

A portion of sodium hydride (17.7 g, 0.44 moles) dispersed in mineral oil is first washed with petroleum ether (b.p. 40-60° C.) and then suspended in 200 mL dry tetrahydrofuran, in a 2 L three-neck flask. A solution of phenothiazine (80.0 g, 0.4 moles) dissolved in tetrahydrofuran (400 mL) is added under argon through a cannula. The mixture is shaken, always under argon, for one hour at room temperature and then for 30 minutes at 50° C. The mixture acquires an orange colour, following the formation of the phenothiazine anion. After the suspension has cooled to 0° C., a solution of 1,3-propanesultone (35 mL, 0.4 moles) in tetrahydrofuran is added also through a cannula. The colour of the mixture changes almost immediately to clear yellow. The mixture is stirred at 0° C. for thirty minutes after the addition of the sultone and then at room temperature for another thirty minutes.

During this period, the mixture becomes almost colourless and homogeneous, with total dissolution of the material in suspension. Subsequently, the product precipitates in crystalline form. At the end of reaction, the product is separated from the solution by means of filtration and washed thoroughly first with tetrahydrofuran and then with ether. Yield: 127.6 g (92.9%). The product is already of high purity. In particular, chromatographic analysis (HPLC, $\lambda=254$ nm) shows that the content of phenothiazine in the product is less than 0.0002 parts (mole/mole). Other impurities can be removed efficiently by recrystallization from ethanol. Molecular mass ($C_{15}H_{14}NaO_3S_2$): 343.40. $^1$H NMR 300 MHz, $D_2O$) δ: 6.9-7.1 (m, 4H, ArH), 6.7-6.9 (m, 4H, ArH), 3.8 (t, 2H, —$CH_2$—N, J=9.9 Hz), 2.5 (t, 2H, —$CH_2$—S, J=11.2 Hz), 1.8-2.0 (m, 2H, —$CH_2$—$CH_2$—$CH_2$). Molecular mass of the free acid ($C_{15}H_{15}O_3S_2$): 321.42. MS (API-ES): 322.0 [MH]$^+$.

Example 2

Synthesis of sodium 4-(phenotiazin-10-yl)butane-1-sulfonate

The synthesis of sodium 4-(phenotiazin-10-yl)butane-1-sulfonate is similar to that described in the previous Example. The only difference lies in that a solution of 1,4-butan sultone (41 mL, 0.40 moles) in tetrahydrofuran (200 mL) is used instead of the solution of 1,3-propanesultone. Again, the product, sodium 4-(phenotiazin-10-yl)butane-1-sulfonate, crystallizes from the reaction mixture. Yield: 122.4 g (85.6%). The product is already of high purity. In particular, chromatographic analysis (HPLC, $\lambda=254$ nm) shows that the content of phenothiazine in the product is less than 0.0002 parts (mole/mole).

Molecular mass ($C_{16}H_{16}NaO_3S_2$): 357.42. $^1$H NMR (300 MHz, $D_2O$) δ: 6.9-7.1 (m, 4H, ArH), 6.7-6.9 (m, 4H, ArH), 3.7 (t, 2H, —$CH_2$—N, J=9.9 Hz), 2.5 (t, 2H, —$CH_2$—$SO_3Na$, J=11.2 Hz), 1.5-1.8 (m, 4H, —$CH_2$—$C_2H_4$—$CH_2$). Molecular mass of the free acid ($C_{16}H_{17}O_3S_2$): 335.44. MS (API-ES): 336.3[MH]$^+$.

Example 3

Dependence of the luminol-peroxide-peroxidase reaction on the concentration of sodium 3-(phenothiazin-10-yl)propane-1-sulfonate All measurements reported in Example 3 were carried out with a spectrofluorimeter (Varian Eclipse), Bio/Chemiluminescence Mode (wavelength of emission: 425 nm; emission slit: 20 nm). A series of substrates in 0.1 M, pH 8.6 Tris Buffer is prepared, with the following compositions:
[luminol sodium salt]=2.50 mM
[sodium perborate]=2.00 mM
3-(phenothiazin-10-yl)propane-1-sulfonate=11.5 μM, 23 μM, 47 μM, 94 μM, 188 μM, 375 μM, 1500 μM e 3000 μM.

To a polymethylmethacrylate fluorimetry cuvette of containing 2 mL of each substrate, is added 10 μL of a solution of 0.5 μg/mL of horseradish peroxidase (HRP-Type VIIA). After mixing the solution with a vortex for a few seconds, measurement of the luminescent signal is initiated. In all cases the chemiluminescent signal reaches a plateau within a few minutes, and then remains stable for at least thirty minutes. The dependence of the chemiluminescent signal (plateau value) for each substrate, is reported graphically in FIG. 1. The luminescent signal grows very rapidly with increasing concentration of the enhancer, 3-(phenothiazin-10-yl)propane-1-sulfonate, until it reaches a maximum value between 0.5 and 1 mM. Further raising the concentration of the enhancer, the chemiluminescent signal begins to decline slowly. At the highest concentration of enhancer, 3.0 mM, the signal is approximately 70% of the maximum value.

Example 4

Figure 2:
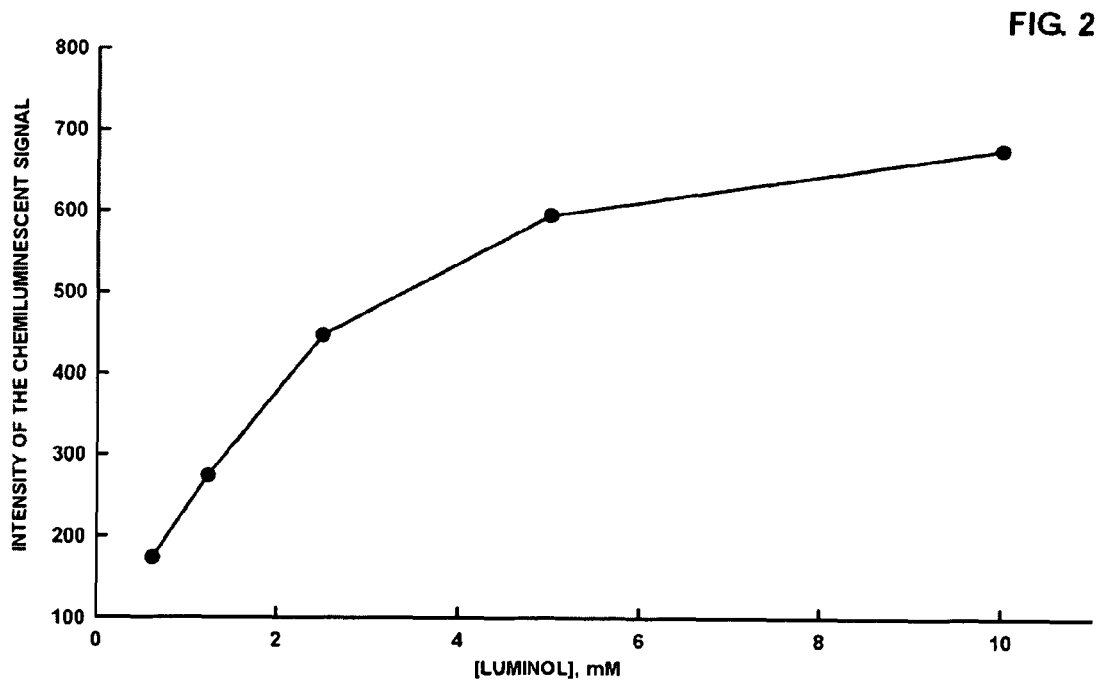
FIG. 2: graph of the chemiluminescent signal as a function of the substrate solution concentration.

Dependence of the sodium 3-(phenothiazin-10-yl)propane-1-sulfonate enhanced luminol-peroxide-peroxidase reaction on luminol concentration All measurements reported in Example 4 were carried out with a spectrofluorimeter (Varian Eclipse), Bio/Chemiluminescence Mode (wavelength of emission: 425 nm; emission slit: 20 nm). A series of substrates in 0.1 M, pH 8.6 Tris Buffer is prepared, with the following compositions:
[luminol sodium salt]=0.625 mM, 1.25 mM, 2.50 mM, 5.0 mM, 10 mM.
[sodium perborate]=2.00 mM
3-(phenothiazin-10-yl)propane-1-sulfonate=0.75 mM To a polymethylmethacrylate fluorimetry cuvette of containing 2 mL of each substrate, is added 10 μL of a solution of 0.5 μg/mL of horseradish peroxidase (HRP-Type VIIA). After mixing the solution with a vortex for a few seconds, measurement of the luminescent signal is initiated. In all cases the chemiluminescent signal reaches a plateau within a few minutes, and then remains stable for at least thirty minutes. The dependence of the chemiluminescent signal (plateau value) for each substrate, is reported graphically in FIG. 2. The luminescent signal gradually grows very rapidly with increasing concentration of the luminol, until it reaches a maximum value between 0.5 and 1 mM. Further raising the concentration of the enhancer, the chemiluminescent signal begins to decline slowly. At the highest concentration of enhancer, 3.0 mM, the signal is approximately 70% of the maximum value. The luminescent signal grows gradually, and reaches a plateau at the highest concentration of luminol used in the experiment, 10 mM.

Figure 3:
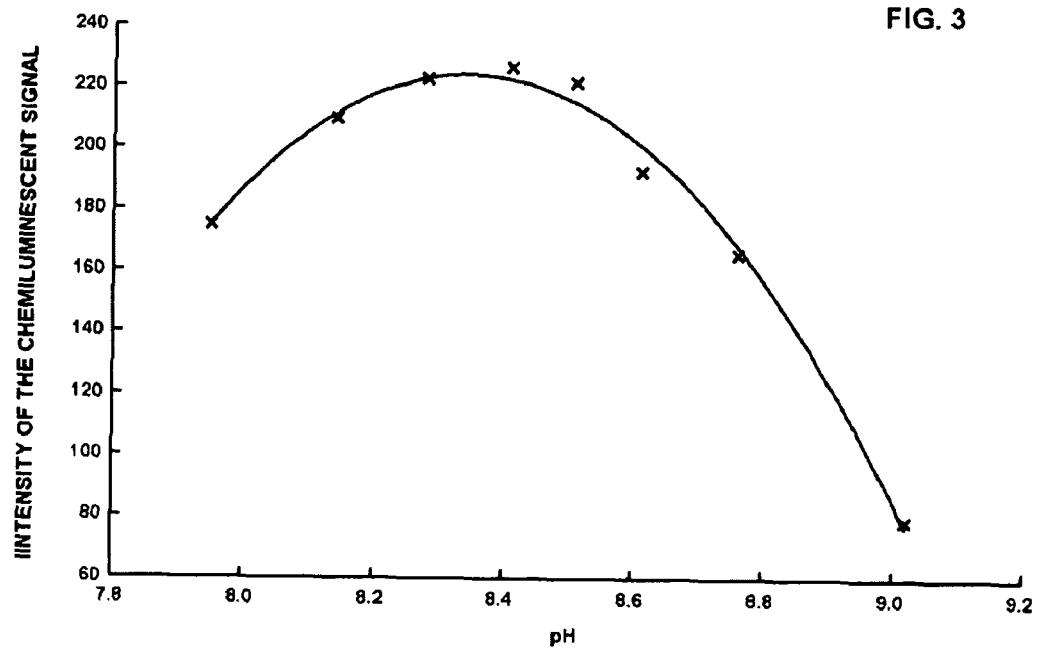
FIG. 3: graph of the chemiluminescent signal as a function of pH.

Example 5 pH dependence of the luminol-peroxide-peroxidase reaction enhanced by sodium 3-(phenotiazin-10-yl)propane-1-sulfonate All measurements reported in Example 5 were carried out with a fluorimeter (Varian Eclipse), Bio/Chemiluminescence Mode (wavelength of emission: 425 nm; emission slit: 10 nm; emission filter: open; photomultiplier voltage: medium). A series of substrates in 0.125 M, pH 9.1 Tris Buffer is prepared, with the following composition:

[luminol sodium salt]=5.0 mM.
[sodium perborate]=4.00 mM
3-(phenothiazin-10-yl)propane-1-sulfonate=1.50 mM A series of polymethylmethacrylate fluorimetry cuvettes is prepared, each containing of containing 2 mL of substrate. To each cuvette is added a small amount of 5M or 12M HCl, in order to adjust the pH to the following values: 9.02, 8.76, 8.51, 8.41, 8.28, 8.14 and 7.95, and limiting changes in the total volume to less than 5%. Then to each cuvette are added 10 μL of a 0.5 μg/mL solution of horseradish peroxidase (HRP-Type VIIA). After mixing the solution with a vortex for a few seconds, measurement of the luminescent signal is initiated. In all cases the chemiluminescent signal reaches a constant value within a few seconds. From the results obtained, which are shown in FIG. 3, it is evident that the chemiluminescent signal reaches the maximum value in the range between pH 8.3 and pH 8.6.

Example 6

Figure 4:
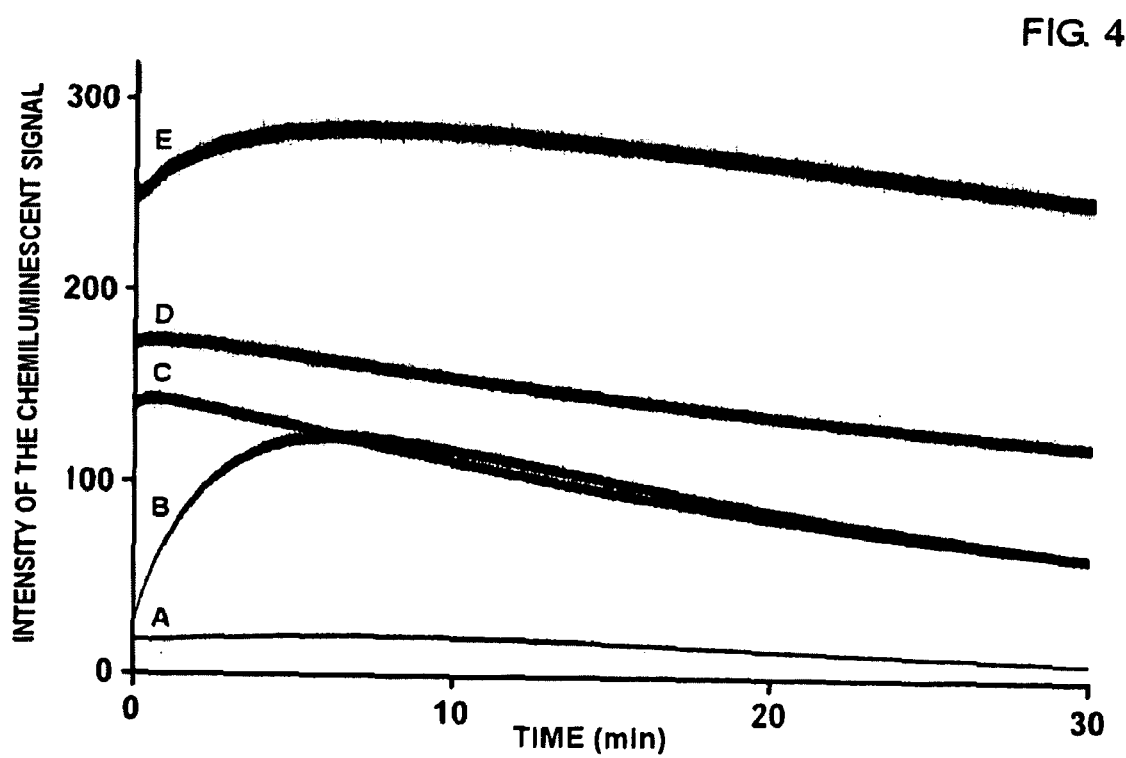
FIG. 4: graph of the chemiluminescent signal as a function of the substrate solution composition.

Comparison between sodium 3-(phenotiazin-10-yl)propane-1-sulfonate, p-iodophenol, p-coumaric acid and 4-iodophenylboronic acid All measurements reported in Example 6 were carried out with a spectrofluorimeter (Varian Eclipse), Bio/Chemiluminescence Mode (wavelength of emission: 425 nm; emission slit: 20 nm). A series of polymethylmethacrylate fluorimetry cuvettes is prepared, each containing 2 mL of the following substrate solution in 0.1 M, pH 8.6 Tris Buffer. 1.25 mM luminol sodium salt, 2.50 mM $H_2O_2$:

Solution A: 0.68 mM p-coumaric acid
Solution B: 0.77 mM 4-iodophenylboronic acid
Solution C: 0.62 mM p-iodophenol
Solution D: 0.75 mM sodium 3-(phenotiazin-10-yl)propane-1-sulfonate It was prepared another substrate, Solution E, with the following composition:

5 mM luminol sodium salt
3 mM sodium 3-(phenotiazin-10-yl)propane-1-sulfonate
4 mM sodium perborate Subsequently, to each cuvette is added 10 μL of a solution of 0.5 μg/mL of horseradish peroxidase (HRP-Type VIIA). After mixing the solution with a vortex for a few seconds, the luminescent signal is measured for 30 min. The results obtained are shown in a graph in FIG. 4.

Example 7

Substrate For Measuring Peroxidase Through Chemiluminescence

A Working Solution (Chemiluminescence Substrate) for measuring Peroxidase can be obtained by mixing equal parts of the following solutions:

Luminol/Enhancer Solution: 10 mM luminol, sodium salt and 6 mM sodium 3-(phenotiazin-10-yl)propane-1-sulfonate (enhancer), prepared as described in Example 1 in 0.3 M, pH 9.6 Tris buffer.
Peroxide Solution: 8 mM Sodium Perborate in 50 mM, pH 5.0 Acetate Buffer Therefore the Working Solution (Chemiluminescence Substrate) contains:

5.0 mM luminolo, sodium salt 5.0 mM
3.0 mM sodium 3-(phenotiazin-10-yl)propane-1-sulfonate
4. mM sodium perborate
0.25 mM sodium acetate in 0.15 mM, pH 8.6 Tris Buffer Tris.

Example 8

Application of the chemiluminescent reaction enhanced by sodium 3-(phenotiazin-10-yl)propane-1-sulfonate to a membrane assay of peroxidase On a sheet of nitrocellulose membrane commonly used for Western Blot assays, cut to approximately 2.5×5.0 cm were spotted 2 μL of solutions containing different concentrations of Horseradish Peroxidase (HRP) in 0.1M, pH 7.4 Tris Buffer additioned with BSA (bovine serum albumin). Each spot was repeated four times. Thus a 4×7 spot matrix was created on the membrane. The membrane was air-dried and washed twice with 0.1 M, pH 7.4 Tris Buffer. Once dry, the membrane was placed on a microscope slide and inserted into an imaging instrument (Nightowl, Berthold Technologies). A Working Solution was then prepared by mixing:

500 μL of solution A prepared as in Example 7
500 μL of solution B prepared as in Example 7 and was sprinkled onto the membrane. Ten second readings were made every 5 minutes for half an hour. The data obtained are shown in the following Table:

| Row No. | Horseradish Peroxidase (μg) | Signal Intensity (4 spot average ± sd) |
|---|---|---|
| 1 | 2.36E−03 | 701 ± 91 |
| 2 | 7.87E−04 | 404 ± 51 |
| 3 | 2.62E−04 | 192 ± 7.2 |
| 4 | 8.74E−05 | 79.8 ± 5.3 |
| 5 | 2.91E−05 | 30.4 ± 1.3 |
| 6 | 9.71E−06 | 19.2 ± 7.8 |
| 7 | 0 | 9.2 ± 2.9 |

These data yield a limit of detection for Horseradish Peroxidase (HRP) of about 10 μg (200 fmol).

Naturally, while the principle of the invention remains the same, the details of construction and the embodiments may widely vary with respect to what has been described and illustrated purely by way of example, without departing from the scope of the present invention.

The invention claimed is:

1. A synthetic process for the preparation of N-alkylsulfonates of phenothiazine of formula (I):

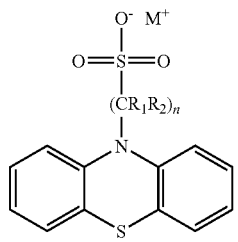

where
M$^+$ is a monovalent, polivalent, organic or inorganic cation,
R$_1$ and R$_2$ are independently from each other H, linear or branched, substituted or unsubstituted alkyl radicals having a number of carbon atoms between 1 and 6, and linear or branched, substituted or unsubstituted alkyl ether radicals having a number of carbon atoms between 1 and 6, and
n is an integer $\geq 2$,
wherein the process comprises the following steps:
  a. the preparation of the anion of phenothiazine,
  b. the reaction of said anion with a cyclic alkylsulfonic ester (sultone),
with precipitation of said N-alkylsulfonates of phenothiazine of formula (I) in crystalline form,
wherein the preparation of the anion of phenothiazine in step a, takes place in situ in a solution containing phenothiazine and an organic solvent by addition of a base, and wherein said cyclic alkylsulfonic ester is a four- to seven-membered ring.

2. The synthetic process for the preparation of N-alkylsulfonates of phenothiazine according to claim 1, wherein R$_1$ and R$_2$ are linear, unsubstituted alkyl radicals having a number of carbon atoms between 1 and 6.

3. The synthetic process for the preparation of N-alkylsulfonates of phenothiazine according to claim 1, wherein R$_1$ and R$_2$ are H and n is equal to 3 or 4.

4. The synthetic process for the preparation of N-alkylsulfonates of phenothiazine according to claim 1, wherein said organic solvent is selected among tetrahydrofuran, diethyl ether, t-butylmethyl ether, dioxane, dimethyl ether of ethylene glycol, diethyl ether of ethylene glycol, dimethyl ether of ethylene diglycol, diethyl ether of ethylene diglycol.

5. The synthetic process for the preparation of N-alkylsulfonates of phenothiazine according to claim 1, wherein said base is selected among sodium hydride, sodium amide, butyl lithium, lithium diisopropylamide.

6. The synthetic process for the preparation of N-alkylsulfonates of phenothiazine according to claim 1, wherein said cyclic alkylsulfonic ester is selected among 1,3-propane sultone, 1,4-butane sultone, 1-(2-ethoxy-1,1,3,3,3-pentafluoro)propane sultone.

7. The synthetic process for the preparation of N-alkylsulfonate of phenothiazine according to claim 1, wherein the phenothiazine content in said N-alkylsulfonate of phenothiazine of formula (I) is less than 0.0002 part (mole/mole).

8. The synthetic process for the preparation of N-alkylsulfonate of phenothiazine according to claim 1, wherein said N-alkylsulfonate of phenothiazine is a sodium salt of 3-(phenothiazin-10-yl)propane-1-sulfonate and said cyclic alkylsulfonic ester is propane sultone.

9. The synthetic process for the preparation of N-alkylsulfonate of phenothiazine according to claim 1, wherein said N-alkylsulfonate of phenothiazine is a sodium salt of 4-(phenothiazin-10-yl)butane-1-sulfonate and said cyclic alkylsulfonic ester is butane sultone.

10. The synthetic process for the preparation of N-alkylsulfonate of phenothiazine according to claim 8, yielding a sodium 3-(phenothiazin-10-yl)propane-1-sulfonate having a phenothiazine content of less than 0.0002 part (mole/mole).

11. The synthetic process for the preparation of N-alkylsulfonate of phenothiazine according to claim 9, yielding a sodium 4-(phenothiazin-10-yl)butane-1-sulfonate having a phenothiazine content of less than 0.0002 part (mole/mole).

12. The synthetic process for the preparation of N-alkylsulfonate of phenothiazine according to claim 1, wherein M$^+$ is selected from H$^+$, Na$^+$, Li$^+$, K$^+$, or NH$_4^+$.

* * * * *

(12) EX PARTE REEXAMINATION CERTIFICATE (9537th)
United States Patent
Della Ciana

(10) Number: US 7,855,287 C1
(45) Certificate Issued: Mar. 1, 2013

(54) PREPARATION OF HIGH PURITY PHENOTHIAZINE N-ALKYLSULFONATES AND THEIR USE IN CHEMILUMINESCENT ASSAYS FOR THE MEASUREMENT OF PEROXIDASE ACTIVITY

(75) Inventor: Leopoldo Della Ciana, Bologna (IT)

(73) Assignee: Cyanagen Srl, Bologna (IT)

Reexamination Request:
No. 90/012,651, Sep. 14, 2012

Reexamination Certificate for:
Patent No.: 7,855,287
Issued: Dec. 21, 2010
Appl. No.: 12/010,306
Filed: Jan. 23, 2008

(30) Foreign Application Priority Data

Jan. 24, 2007 (IT) ............... BO2007A0037

(51) Int. Cl.
*C07D 279/26* (2006.01)
(52) U.S. Cl. ............... 544/35; 544/38
(58) Field of Classification Search ............... None
See application file for complete search history.

(56) References Cited

To view the complete listing of prior art documents cited during the proceeding for Reexamination Control Number 90/012,651, please refer to the USPTO's public Patent Application Information Retrieval (PAIR) system under the Display References tab.

*Primary Examiner* — Gary Kunz

(57) ABSTRACT

A process is described for preparing, efficiently and with a high degree of purity N-alkylsulfonates of phenothiazine. The process consists in (a) the preparation of the phenothiazine anion, and (b) the reaction of said anion with cyclic alkyl sulfonates, such as 1,3-propane sultone and 1,4-butane sultone. This process is simpler, more direct, and more efficient than the procedures currently used for the synthesis of N-alkylsulfonates derivatives of phenothiazine. In addition, the products obtained with this process are far more pure than those obtained through current procedures and therefore ideal for bioanalytical applications that require high sensitivity, such as assays based on the measurement of peroxidase activity using chemiluminescence.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-12 is confirmed.

* * * * *